(12) United States Patent
Itoh et al.

(10) Patent No.: US 6,528,635 B1
(45) Date of Patent: Mar. 4, 2003

(54) TUMOR ANTIGEN PROTEIN, GENE THEREOF, AND UTILIZATION THEREOF

(75) Inventors: Kyogo Itoh, 2-25-9, Keyaki-dai, Kiyama-cho, Miyaki-gun, Saga-ken (JP); Shigeki Shichijo, Kurume (JP); Yasuhisa Imai, Kurume (JP)

(73) Assignee: Kyogo Itoh, Saga-ken (JP)

(*) Notice: Subject to any disclaimer, the term of this patent is extended or adjusted under 35 U.S.C. 154(b) by 0 days.

(21) Appl. No.: 09/582,324

(22) PCT Filed: Dec. 22, 1998

(86) PCT No.: PCT/JP98/05809

§ 371 (c)(1),
(2), (4) Date: Aug. 11, 2000

(87) PCT Pub. No.: WO99/33977

PCT Pub. Date: Jul. 8, 1999

(30) Foreign Application Priority Data

Dec. 25, 1997 (JP) .............................................. 9-356895

(51) Int. Cl.⁷ .............................................. C07H 21/04
(52) U.S. Cl. .................. 536/23.5; 536/23.1; 435/320.1; 435/325; 435/69.1; 435/70.1; 530/350; 530/300
(58) Field of Search ............................... 536/23.1, 23.5; 530/350; 424/184.1, 277.1, 185.1; 435/320.1, 325, 70.1, 69.1; 514/2, 12

(56) References Cited

U.S. PATENT DOCUMENTS 5,356,817 A * 10/1994 Cole ............................ 436/64

FOREIGN PATENT DOCUMENTS

| EP | 0911397 A1 | * 12/1997 | ............ C12N/15/12 |
| EP | 0911397 | 4/1999 | |
| JP | WO-97/46676 | * 12/1997 | ............ C12N/15/12 |
| WO | A1-9746676 | 12/1997 | |

OTHER PUBLICATIONS

Gura (Science, 1997, 278:1041–1042).*
Jain (Sci. Am., 1994, 271:58–65).*
Curti (Crit. Rev. in Oncology/Hematology, 1993, 14:29–39).*
Hartwell et al (Science, 11997, 278:64–1068).*
Ito et al (EMBL AB006198, Aug. 4, 1997).*
Valenta et al (EMBL Y14314, Jul. 23, 1997).*
Bodey, B, et al, 2000, Failure of cancer vaccines: the significant limitations of this approach to immunotherapy, Anticancer Research, vol. 20, pp. 2665–2676.*
Lee, K–H, et al, 1999, Increased vaccine–specific T cell frequency after peptide–based vaccination correlates with increased susceptibility to in vitro stimulation but does not lead to tumor regression, Journal of Immunology, vol. 163, pp. 6292–6300.*
Zaks, TZ, et al, 1998, Immunization with a peptide epitope (p369–377) from HER–2/neu leads to peptide–specific cytotoxic T lymphocytes that fail to recognize HER–2/neu+ tumors, Cancer Research, vol. 58, pp. 4902–4908.*
Ezzell, C, 1995, Cancer "vaccines": an idea whose time has come?, Journal of NIH Research, vol. 7, pp. 46–49.*
Splitler, LE, 1995, Cancer vaccines: the interferon analogy, Cancer Biotherapy, vol. 10, No. 1, pp. 1–3.*
Arceci, RJ, 1998, The potential for antitumor vaccination in acute myelogenous leukemia, Journal of Molecular Medicine, vol. 76, pp. 80–93.*
Tockman, MS, et al, 1992, Considerations in bringing a cancer biomarker to clinical application, Cancer Research, vol. 52, Suppl., pp. 2711s–2718s.*
Boon, T, 1992, Toward a genetic analysis of tumor rejection antigens, Advances in Cancer Research, vol. 58, pp. 177–210.*
Ward, AM, 1985, Tumour Markers, Developmental Oncology, vol. 21, pp. 90–106 (abstract only; CANCERLIT Database Accession No. 86620633).*
Shichijo, S., et al., "Journal of Experimental Medicine", vol. 187, No. 3 pp. 277–278 (1998).
Masanobu Nakao et al., Cancer Research, vol. 55, Oct. 1, 1995, pp. 4248–4252.
Thierry Boon et al., J. Exp. Med., vol. 183, Mar. 1996, pp. 725–729.

* cited by examiner

Primary Examiner—Anthony C. Caputa
Assistant Examiner—Stephen L. Rawlings
(74) Attorney, Agent, or Firm—Birch, Stewart, Kolasch & Birch, LLP

(57) ABSTRACT

A DNA consisting of the base sequence represented by SEQ ID NO: 1 or a DNA hybridizing with a DNA consisting of the base sequence represented by SEQ ID NO: 1 under stringent conditions and encoding a protein having activities as a tumor antigen; an expression plasmid containing the above DNA; a transformant transformed therewith; a tumor antigen protein produced as a result of expression of the above DNA; an antibody against the above protein; and the use thereof in the treatment, prevention or diagnosis of tumors.

6 Claims, 2 Drawing Sheets

A

B

TUMOR ANTIGEN PROTEIN, GENE THEREOF, AND UTILIZATION THEREOF

This application is the national phase under 35 U.S.C. §371 of PCT International Application No. PCT/JP98/05809 which has an International filing date of Dec. 22, 1998, which designated the United States of America.

TECHNICAL FIELD

The present invention relates to novel tumor antigen proteins and genes encoding the same, and antibodies against said tumor antigen proteins, as well as methods of treating, preventing, or diagnosing tumors using such materials.

BACKGROUND ART

It is known that the immune system, particularly T cells, plays an important role in vivo in tumor rejection. Indeed, infiltration of lymphocytes having cytotoxic effects on tumor cells has been observed in human tumor foci (*Arch. Surg.,* 126:200–205, 1990), and cytotoxic T lymphocytes (CTLs) recognizing autologous tumor cells have been isolated from melanomas without great difficulties (e.g., *Immunol. Today,* 8:385, 1987; *J. Immunol.,* 138:989, 1987; and *Int. J. Cancer,* 52:52–59, 1992). In addition, the results of clinical treatment of melanomas by T cell introduction also suggest the importance of T cells in tumor rejection (*J. Natl. Cancer. Inst.,* 86:1159, 1994).

Although it has long been unknown about target molecules for CTLs attacking autologous tumor cells, the recent advance in immunology and molecular biology has gradually revealed such target molecules. Specifically, it has been found that using T cell receptors (TCRs), CTL recognizes a complex between a peptide, called tumor antigen peptide, and a major histocompatibility complex class I antigen (MHC class I antigen, and in the case of human, referred to as HLA antigen), and thereby attacks autologous tumor cells.

Tumor antigen peptides are generated from proteins specific for tumors, that is, tumor antigen proteins. Thus, the proteins are intracellularly synthesized and then degraded in cytoplasm into the peptides by proteasome. On the other hand, MHC class I antigens (HLA antigens) formed at endoplasmic reticulum, when bind to the above tumor antigen peptides, are transported via cis Golgi to trans Golgi, i.e., the mature side and carried to the cell surface where they are presented as an antigen. A tumor-specific CTL recognizes this complex presented as an antigen, and exhibits its anti-tumor effects through the cytotoxic effect or production of lymphokines (*Rinsho-Menneki,* 27(9):1034–1042, 1995). As a consequence of such elucidation of a series of actions, it has become possible to treat tumors by using tumor antigen proteins or tumor antigen peptides as so-called cancer vaccines which enhance tumor-specific CTLs in a patient.

As such tumor antigen proteins, T. Boon et al. identified a protein named MAGE from human melanoma cells for the first time in 1991 (*Science,* 254:1643–1647, 1991), and thereafter several additional tumor antigen proteins have been identified from melanoma cells.

As reviewed by T. Boon et al. (*J. Exp. Med.,* 183, 725–729, 1996), tumor antigen proteins hitherto identified can be divided into the following four categories.

Tumor antigen proteins belonging to the first category are those which are expressed in testis only as normal tissues, while they are expressed in melanoma, head and neck cancer, non-small cell lung cancer, bladder cancer and others, as tumor tissues. Among tumor antigen proteins in this category are the above-described MAGE and analogous proteins constituting a family of more than 12 members (*J. Exp. Med.,* 178:489–495, 1993), as well as BAGE (*Immunity,* 2:167–175, 1995) and GAGE (*J. Exp. Med.,* 182:689–698, 1995), all of which have been identified in melanoma cells.

Although some of such tumor antigen proteins in this category are highly expressed in melanoma, the expression thereof is observed in only 10 to 30% of patients having a particular tumor other than melanoma, and therefore, they cannot be applied widely to treatments or diagnoses of various tumors.

Tumor antigen proteins belonging to the second category are those which are expressed only in melanocytes and retina among normal tissues, and in melanomas among tumor tissues. Since these tissue-specific proteins are highly expressed in melanomas, they would function as tumor antigen proteins specific for melanomas, Among tumor antigen proteins in this category are tyrosinase (*J. Exp. Med.,* 178:489–495, 1993), MART-1 (*Proc. Natl. Acad. Sci. USA,* 91:3515, 1994), gp100 (*J. Exp. Med.,* 179:1005–1009, 1994), and gp75 (*J. Exp. Med.,* 181:799–804, 1995). Genes encoding these proteins have all been cloned from melanoma cells. Melan-A (*J. Exp. Med.,* 180:35, 1994), which has been separately isolated, has proved to be identical with MART-1.

However, the tumor antigen proteins of this category cannot be used widely in the treatments or diagnoses of various tumors, since they are not expressed in tumors other than melanoma.

Tumor antigen proteins belonging to the third category are those which are expressed as tumor antigen peptides recognized by CTL as a result of tumor-specific mutations. Among tumor antigen proteins in this category are mutated CDK4 (*Science,* 269:1281–1284, 1995), β-catenin (*J. Exp. Med.,* 183:1185–1192, 1996), and MUM-1 (*Proc. Natl. Acad. Sci. USA,* 92:7976–7980, 1995). In CDK4 and β-catenin, a single amino acid mutation increases the binding affinity of the peptides to MHC class I antigen, which allows them to be recognized by T cells. In MUM-1, an intron, which normally is not translated, is translated due to mutation, and the resultant peptide is recognized by T cells. However, since such mutations occur at low frequency, they cannot be applied widely to treatments or diagnoses of various tumors.

Tumor antigen proteins belonging to the fourth category are those widely expressed in normal tissues and also recognized by CTL, example of which includes P15 identified from melanoma cells (*J. Immunol.* 154:5944–5955, 1995).

Some of known tumor antigen proteins as described above are expressed only in limited tumors such as melanoma, and the others are expressed only in a small number of patients having a particular tumor even if they are expressed in various kinds of tumor, and therefore, they cannot be used widely in the treatments or diagnoses of various tumors. Accordingly, it is necessary to identify a tumor antigen that is widely applicable to various tumors, for instance, squamous cell carcinomas (e.g., esophageal cancer, lung cancer), which show much higher incidence than melanomas, before the application of tumor antigen proteins or tumor antigen peptides generated therefrom by intracellular degradation to the treatments or the diagnoses of various tumors. In this connection, the present inventors have conducted cloning of a gene encoding a tumor antigen protein from squamous cell carcinoma cells derived from esophageal cancer, and, for the first time, succeeded in cloning a gene encoding a tumor antigen protein (SART-1) from tumor cells other than melanomas (International Publication WO 97/46676).

Regarding diagnosis of tumors, various approaches are now being made by means of antibodies against tumor associated antigens, which, for example, include detection of antigenic substances in blood by radioimmunoassay, ELISA, or the like; histological cytodiagnosis by immunohistochemical methods such as enzyme-linked immunosorbent assay or fluorescent antibody technique; or imaging of tumors (Fishman, W. H. et al., "Oncodevelopmental Markers", Academic Press, 1983). However, leading tumor markers currently used give a false positive in benign diseases with relatively high frequency. Therefore, there has been a great demand for the identification of a tumor antigen protein highly specific for tumors and the isolation of antibodies against the same to be used in diagnosis.

Furthermore, when using a particular tumor antigen protein or tumor antigen peptide as, for example, a vaccine, it is desired that a patient who expresses the tumor antigen protein and is possibly reactive to treatment with the tumor antigen protein/peptide is diagnosed and selected before applying the protein/peptide to the patient. Tumor antigen proteins with high tumor specificity or antibodies directed thereto are believed to be extremely useful diagnostic agents in the selection of such subject patients. From this point of view, it is desired to identify a tumor antigen protein having higher tumor specificity and is applicable to a wide range of tumor patients, and also an antibody raised against the same.

DISCLOSURE OF INVENTION

One of purposes of the present invention is to provide a novel tumor antigen protein or gene, or antibodies against the tumor antigen protein. It is also a purpose of the invention to provide a method of treating, preventing, or diagnosing tumors using such substances. More particularly, the present invention aims to provide a tumor antigen protein highly specific for tumors or corresponding tumor antigen peptides, DNAs encoding them, and antibodies recognizing and binding them, all of which are widely applicable to treatment or diagnosis of various tumors, especially squamous cell carcinomas.

To this end, the present inventors established a squamous cell carcinoma cell line KE-4 derived from esophageal cancer (hereinafter referred to as an esophageal cancer cell line KE-4 or simply as KE-4), and also established CTL (hereinafter referred to as KE-4CTL) which recognizes tumor antigen peptides restricted to HLA-A2601 and HLA-A2402 which are MHC class I antigens expressed in said KE-4 (*Cancer Res.*, 55:4248–4253, 1995).

Fibroblast cell line VA-13 cells were then co-transfected with a recombinant plasmid of cDNA library prepared from KE-4 and a recombinant plasmid containing HLA-A2601 cDNA. The transfectants were then treated with KE-4CTL and screened for the activation of KE-4CTL by measuring the amount of IFN-γ produced. After carrying out the screening repeatedly, the inventors have succeeded in cloning a gene encoding a novel tumor antigen protein. The nucleotide sequence of the cloned gene is shown in SEQ ID NO: 1.

The present inventors then inserted the gene encoding a novel tumor antigen protein into a plasmid vector for expressing a fusion protein with GST, transformed *E. coli* cells with the resultant vector, and prepared a fusion protein between GST and the novel tumor antigen protein of the present invention. Various cell lines and tissues were analyzed by Western blot analysis using antibodies obtained by immunizing a rabbit with the above fusion protein. As a result, expression of the novel tumor antigen protein of the present invention having a molecular weight of about 43 kilo Dalton (kD) was observed in 100% of head and neck squamous cell cancers, 60% of esophageal squamous cell cancers, 50% of lung squamous cell cancers, and 50% of lung adenocarcinomas examined, although no expression was observed in any of all normal tissues except for testis and fetal liver, melanomas, and leukemia. It was also demonstrated that cancer cells which were positive in the Western blot analysis (cancer cells expressing the tumor antigen protein of the present invention) are indeed recognized and damaged by tumor specific CTLs.

As described above, since the tumor antigen protein of the present invention is expressed specifically and with high frequency in various squamous cell cancers and adenocarcinomas, it should be useful as a pharmaceutical for activating the antitumor immunity of patients suffering from such cancers. Further, antibodies against the tumor antigen protein of the present invention should be effectively used in diagnosis of cancer patients and selection of subject patients.

The nucleotide sequence of DNA encoding about 43 kDa tumor antigen protein of the present invention corresponds to the nucleotide sequence beginning at position 1517 of DNA encoding the tumor antigen protein, SART-1, which is described in the International Publication WO 97/46676 (shown as SEQ ID NO: 2 in WO 97/46676). However, the tumor antigen protein of the present invention is believed to be expressed in vivo (in tumor tissues or tumor cells) independently of SART-1, because it was detected in various tumor tissues and tumor cells as a protein having a molecular weight of about 43 kDa in the above-mentioned Western blot analysis and, further, it shows an expression pattern inconsistent with that of SART-1 presumably having a molecular weight of about 125 kD.

The present invention was established on the basis of these findings.

Thus, the present invention relates to a DNA (a) or (b) below:

(a) a DNA consisting of the base sequence shown in SEQ ID NO: 1; or (b) a DNA that hybridizes under stringent conditions to a DNA consisting of the base sequence shown in SEQ ID NO: 1 and that encodes a protein having activity as a tumor antigen.

The present invention also relates to expression plasmids containing said DNA, tumor antigen proteins obtainable through expression of said DNA, antibodies that recognize said tumor antigen proteins, and use thereof.

BRIEF DESCRIPTION OF DRAWING

In FIG. 2A, "Factor Xa (−)" indicates that the fusion protein between the tumor antigen protein of the present invention and GST was not treated with Factor Xa, while "Factor Xa (+)" indicates that the fusion protein was cleaved by treating with Factor Xa. In FIG. 2B, PBMC indicates healthy human peripheral blood monocyte; KE-4 and TE-9 indicate esophageal cancer cell lines; E95-24, E96-18, E96-34, E96-26 and E96-30 indicate esophageal cancer tissues; and KL79, KL80, KL81, KL82, KL83 and KL84 indicate lung cancer tissues.

BEST MODE FOR CARRYING OUT THE INVENTION

Figure 1:
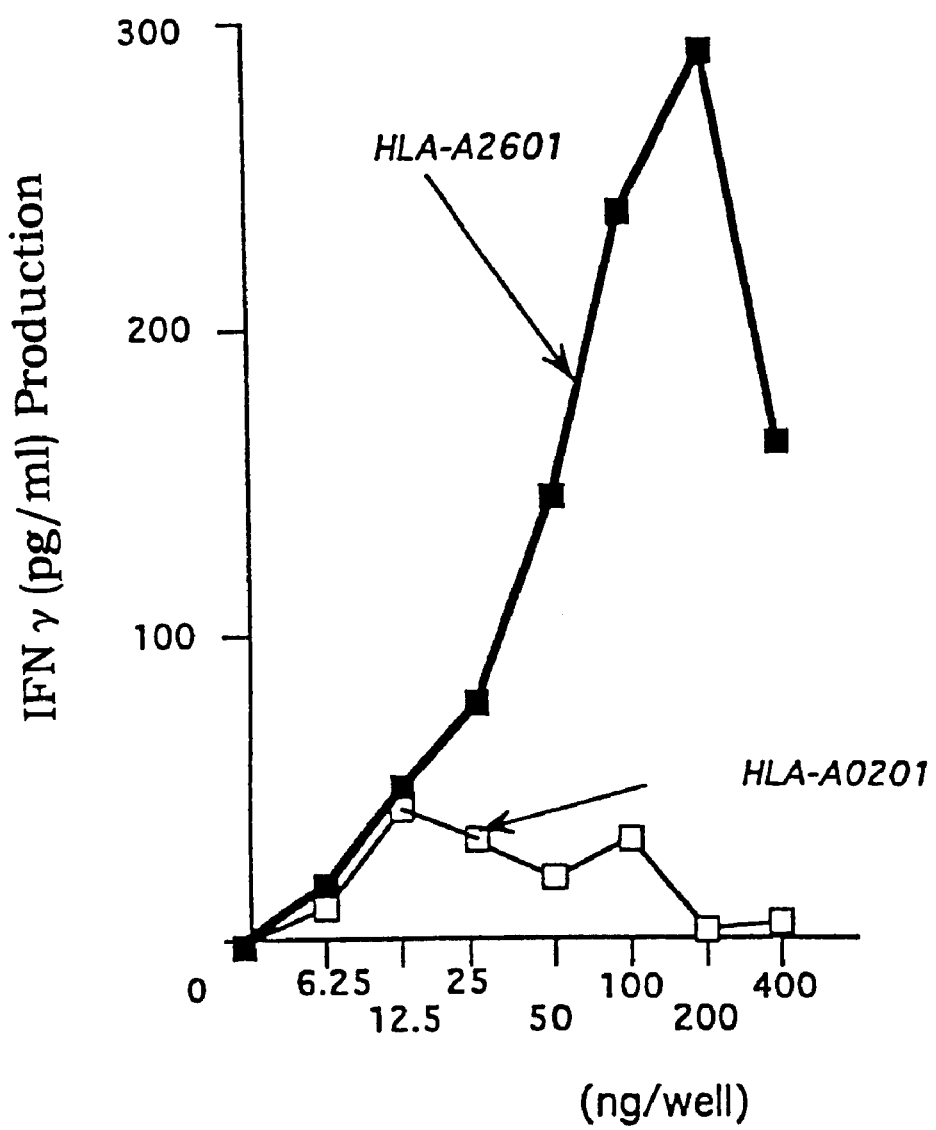
FIG. 1 is a graph showing the results of measurements wherein VA-13 cells were doubly transfected with a gene encoding the novel tumor antigen protein of the present invention and cDNA for HLA-A2601, and cultured together with CTL (KE-4CTL) recognizing HLA-A2601-, HLA-A2402-restricted tumor antigen peptides, and the amount of IFN-γ (■) produced in the medium by KE4-CTL in response thereto was measured. The symbol "□" shows the results obtained by conducting a similar measurements using cDNA encoding an HLA of different type (HLA-A0201 cDNA) in the double transfection for comparison. The vertical axis indicates the amount of IFN-γ, and the horizontal axis indicates the amount of the transfected gene encoding the novel tumor antigen protein.

In this specification, the term "DNA of the present invention" refers to a DNA that encodes a novel tumor antigen protein and that consisting of the base sequence shown in SEQ ID NO: 1, or a DNA that hybridizes under stringent conditions to DNA consisting of the base sequence shown in the SEQ ID NO: 1 and that encodes a protein having activity as a tumor antigen. Furthermore, in this specification, the terms "gene" and "DNA" are used interchangeably when describing a DNA encoding a desired protein having the tumor antigen activity of the present invention.

A "DNA consisting of the base sequence shown in SEQ ID NO: 1" can be cloned according to the method described hereinafter in Examples. Alternatively, it can be cloned by screening a cDNA library derived from, for example, an esophageal cancer cell lines KE-4 (FERM BP-5955) using all or part of the base sequence shown in SEQ ID NO: 1 as a hybridization probe or PCR primer. Those skilled in the art can easily carry out such cloning by reference to a standard textbook such as "Molecular Cloning: A Laboratory Manual", 2nd Ed., vols. 1–3, Cold Spring Harbor Laboratory Press, 1989.

Furthermore, the base sequence shown in SEQ ID NO: 1 corresponds to the sequence at and after position 1517 of DNA encoding the tumor antigen protein, SART-1, which is described in the International. Publication WO 97/46676 of the PCT application by the present applicant (shown as SEQ ID NO: 2 in WO 97/46676). E. coli JM109(K3) containing a DNA encoding said SART-1 has been deposited at The National Institute of Bioscience and Human Technology at 1-1-3 Higashi, Tsukuba, Ibaraki, Japan (Deposition No. FERM BP-5951, deposition date: May 22, 1997). Accordingly, one can obtain a DNA consisting of the base sequence shown in SEQ ID NO: 1 by means of the plasmid included in the deposited microorganism.

As used herein, a "DNA that hybridizes under stringent conditions to a DNA consisting of the base sequence shown in SEQ ID NO: 1" refers to a DNA which has a base sequence similar to that of a DNA consisting of the base sequence shown in SEQ ID NO: 1 and hybridizes thereto under stringent conditions. Examples include a DNA that contains substitution, deletion, and/or addition of one or more bases in a DNA consisting of the base sequence shown in SEQ ID NO: 1.

The said DNA can be obtained by screening various cDNA libraries with a part of DNA consisting of the base sequence shown in SEQ ID NO: 1 as a probe or a primer, according to a method described in, for example, "Molecular Cloning: A Laboratory Manual", 2nd Ed., vols. 1–3, Cold Spring Harbor Laboratory, 1989. Alternatively, a DNA, as described above, that contains substitution, deletion, and/or addition of one or more bases in a DNA consisting of the base sequence shown in SEQ ID NO: 1 may also be prepared by site-directed mutagenesis or PCR method described in the above-mentioned "Molecular Cloning".

In this context, the term "stringent conditions" refers to, for example, such conditions that hybridization is conducted at 42° C. in a solution containing 6×SSC (20×SSC means 333 mM sodium citrate and 333 mM NaCl), 0.5% SDS, and 50% formamide, followed by washing in a solution of 0.1×SSC and 0.5% SDS at 68° C., or those conditions described in Nakayama et al., "Bio-Jikken-Illustrated", vol. 2, "Idenshi-Kaiseki-no-Kiso (Basis for Gene Analysis)", pp. 148–151, Shujunsha, 1995.

As used herein, the phrase "having activity as a tumor antigen" means that the protein has a specific characteristic of being intracellularly degraded to generate a tumor antigen peptide that is bound to MHC class I antigen (HLA antigen) and recognized by CTL. Accordingly, "DNA encoding a protein having activity as a tumor antigen" refers to a DNA that, when expressed, can provide a tumor antigen peptide as a result of intracellular degradation, which peptide is bound to MHC class I antigen (HLA antigen) and recognized by CTL. Thus, when such a DNA is expressed, the resultant protein is degraded intracellularly to give a partial peptide capable of binding to MHC class I antigen. The resultant partial peptide fragment forms a complex with MHC class I antigen and presented on the cell surface, which complex will then be bound by a specific CTL, resulting in the cytotoxic effects and the induction of cytokines. A DNA encoding a protein that generates such a peptide fragment is the "DNA encoding a protein having activity as a tumor antigen" of the present invention.

It can be determined whether a candidate DNA may be a "DNA encoding a protein having activity as a tumor antigen", for example, by the following method.

Firstly, an expression plasmid containing a candidate DNA and another expression plasmid containing DNA encoding MHC class I antigen are doubly transfected into cells not expressing tumor antigen proteins such as COS-7 (ATCC CRL 1651) derived from African green monkey kidney, or fibroblast VA-13 (RIKEN CELL BANK, The Institute of Physical and Chemical Research). The transfection may be achieved, for example, by Lipofectin method using Lipofectamine reagent (GIBCO BRL). Subsequently, a tumor-responsive CTL that is restricted to the particular MHC class I antigen used is added to the transfectants for reaction, and the amount of various cytokines (for example, IFN-γ) produced by said CTL in response is measured by, for example, ELISA to determine whether the candidate DNA is the one which encodes a protein having activity as a tumor antigen. An expression plasmid that contains DNA encoding a particular MHC class I antigen may be prepared, for example, according to a known method (Nakao et al., Cancer Res., 55:4248–4252 (1995)).

By using the DNA of the present invention, a tumor antigen protein can be produced in large quantities according to the recombinant DNA technique. The production of tumor antigen protein through expression of DNA of the present invention can be carried out according to the descriptions in many publications and literatures such as "Molecular Cloning" mentioned above. An expression plasmid which replicates and is expressed in host cells can be constructed by inserting a DNA to be expressed into an appropriate vector (e.g., pSV-SPORT1), optionally after ligating a regulatory gene(s) such as a promoter which controls transcription (e.g., trp, lac, T7, or SV40 early promoter) upstream to the DNA. The expression plasmid is then introduced into appropriate host cells to obtain transformants. Examples of host cell include prokaryotes such as *Escherichia coli*, unicellular eukaryotes such as yeast, and cells derived from multicellular eukaryotes such as insects or animals. Transformation of host cells with an expression plasmid can be carried out by a known method such as the calcium phosphate method, DEAE-dextran method, or the electric pulse method. The resultant transformants, when cultured by a usual method in a medium suitable for the transformants, produce the desired protein. The tumor antigen protein thus obtained can be isolated and purified according to standard biochemical procedures.

Furthermore, a DNA encoding the tumor antigen protein of the present invention can be inserted into a plasmid vector for expression of a fusion protein with, for example, GST (glutathione S-transferase) (e.g., pGEX-5X-3, Pharmacia Biotech), and the resulting expression vector may also be used. For example, when a host such as *E. coli* strain DH5α is transformed with such an expression vector, the resultant transformants can produce a fusion protein between the tumor antigen protein of the present invention and GST. The fusion protein can easily be purified by, for example, Glutathione Sepharose. Although the purified fusion protein may have the above-mentioned activity as a tumor antigen, it is desired to obtain a non-fused tumor antigen protein by separating the GST moiety with an enzyme Factor X or the like.

The expression product is a protein coded by a DNA of the present invention and is produced as a result of its expression. Accordingly, the protein has the characteristic, as a tumor antigen protein, of being intracellularly degraded to generate a tumor antigen peptide that is bound to MHC class I antigen and recognized by CTL.

The present invention also provides expression plasmids containing a DNA consisting of the base sequence shown in SEQ ID NO: 1 or DNA that hybridizes under stringent conditions to a DNA consisting of the base sequence shown in SEQ ID NO: 1 and encodes a protein having activity as a tumor antigen.

In addition, the present invention provides transformants that have been transformed by said expression plasmid.

Furthermore, the present invention provides proteins having activity as a tumor antigen that may be produced by expression of the above DNA of the present invention.

One specific example of such protein is a protein that is obtainable through expression of DNA consisting of the base sequence shown in SEQ ID NO: 1. In SDS-PAGE under reducing conditions, this protein shows a band at a molecular weight of about 43 kD.

In one embodiment, a tumor antigen protein of the present invention comprises the amino acid sequence shown in SEQ ID NO: 2. The amino acid sequence shown in SEQ ID NO: 2 is encoded by a segment of the base sequence shown in SEQ ID NO: 1 from position 590 to position 922, and contains at least its HLA-A26- and HLA-A24-restricted tumor antigen peptide portions.

As described above, the base sequence shown in SEQ ID NO: 1 corresponds to the sequence at and after position 1517 of DNA encoding the tumor antigen protein, SART-1, which is disclosed by the present inventors and described in the International Publication WO 97/46676 (shown as SEQ ID NO: 2 in the International Publication WO 97/46676). Likewise, the amino acid sequence shown in SEQ ID NO: 2 corresponds to the sequence at and after position 690 of the amino acid sequence of said SART-1 (shown as SEQ ID NO: 1 in the International Publication WO 97/46676), and it has been demonstrated by the present inventors that various tumor antigen peptide portions reside in this partial sequence at and after position 690 (see the International Publication WO 97/46676).

The aforementioned tumor antigen proteins and genes (DNAs) therefor of the present invention are useful in vivo and in vitro for various purposes including treatment, prophylaxis, and diagnosis of tumors, as described below in detail. In particular, DNAs of the present invention and their expression products, that is, tumor antigen proteins can be widely used as anti-tumor drugs or diagnostic agents for frequently occurring cancers such as squamous cell carcinomas. In this connection, squamous cell carcinoma is one of the most frequently occurring human cancers, and particularly, it is known that squamous cell carcinoma in esophageal or lung cancer is relatively resistant to current chemotherapy or radiotherapy.

Thus, the present invention provides pharmaceuticals that comprise as an active ingredient the DNA or tumor antigen protein of the present invention.

Pharmaceuticals that comprise as an active ingredient the tumor antigen protein of the present invention may be administered together with adjuvants so as to effectively establish the cellular immunity, or in particulate dosage form. When the tumor antigen protein is administered to a living body, tumor antigen peptides are presented at high density on MHC class I antigens of antigen-presenting cells, which leads to the efficient proliferation of tumor-specific CTLs and the accomplishment of treatment or prevention of tumor. For such a purpose, adjuvants described in the literature (*Clin. Microbiol. Rev.*, 7:277–289, 1994) are applicable. In addition, dosage forms which allow foreign antigen peptides to be efficiently presented on MHC class I antigen, such as liposomal preparations, particulate preparations in which the tumor antigen protein or the peptides are bound to beads having a diameter of several µm, or preparations in which the protein or peptides are attached to lipids, are also contemplated. Administration may be achieved, for example, intradermally, hypodermically, or by intravenous injection. It is also contemplated a method wherein antigen presenting cells such as dendritic cell or macrophage presenting the tumor antigen peptides, or cells into which DNA encoding the tumor antigen protein has been introduced are administered. Although the amount of the tumor antigen protein of the present invention in the formulation for administration may be adjusted as appropriate depending on, for example, the disease to be treated, the age and the body weight of a particular patient, it would usually be from 0.0001 mg to 1000 mg, preferably from 0.001 mg to 1000 mg and is preferably administered at every several days to every several months.

Tumors can be treated or prevented by administering pharmaceuticals that contain, as an active ingredient, DNA encoding the tumor antigen protein of the present invention to patients suffering from a tumor(s). When DNA of the present invention is administered, the tumor antigen proteins are expressed in the cells to great extent, and the resultant tumor antigen peptides bind to MHC class I antigen, and presented on the cell surface at high density. This will cause efficient proliferation of tumor-specific CTLs in the body, thereby accomplishing the treatment or prevention of the tumor. The methods of administering, and introducing DNA into cells for such purposes are known in the art. Examples of a method include one which employs viral vectors and those described in literatures (*Nikkei-Science,* April, 1994, pp. 20–45; *Gekkan-Yakuji,* 36(1), 23–48 (1994); *Jikken-Igaku-Zokan,* 12(15), 1994, and references cited therein), and any of such methods may be applied to the present invention.

Examples of methods which use viral vectors include those wherein the DNA of the present invention is incorporated into DNA or RNA virus such as retrovirus, adenovirus, adeno-associated virus, herpesvirus, vaccinia virus, poxvirus, poliovirus, or Sindbis virus, and then introduced into cells. Among them, the methods using retrovirus, adenovirus, adeno-associated virus, or vaccinia virus are particularly preferred.

Further, there is another method wherein expression plasmids are directly injected intramuscularly (DNA vaccination), the liposome method, Lipofectin method, microinjection, the calcium phosphate method, and electroporation. Among them, DNA vaccination and the liposome method are particularly preferred.

In order to make DNA of the present invention act as pharmaceutical in practice, one can use either of two methods: in vivo method in which DNA is directly introduced into the body, or ex vivo method in which certain kinds of cells are removed from human, and after introducing DNA into said cells outside of the body, reintroduced into the body (*Nikkei-Science,* April, 1994, pp. 20–45; *Gekkan-Yakuji,* 36(1), 23–48 (1994); *Jikkenn-Igaku-Zokan,* 12(15), 1994; and references cited therein). In vivo method is rather preferred, although DNA of the present invention may be administered by either method.

In the case of in vivo methods, DNA may be administered via any appropriate route depending on the diseases and symptoms to be treated, and other factors. For example, it may be administered via intravenous, intraarterial, subcutaneous, intracutaneous, or intramuscular routes. In the case of in vivo methods, such pharmaceuticals may be administered in various dosage forms such as solution, and they are typically formulated into injections containing DNA of the present invention as an active ingredient, which may also include, as needed, conventional carriers. When DNA of the present invention is included in liposomes or membrane-fused liposomes (such as Sendai virus (HVJ)-liposomes), such medicines may be in the form of suspension, frozen drug, centrifugally-concentrated frozen drug or the like.

Although the amount of DNA of the present invention in such formulations varies depending on, for example, the disease to be treated, the age and body weight of a particular patient, it is usually preferred to administer 0.0001–100 mg, more preferably 0.001–10 mg, of DNA of the present invention at every several days to every several months.

Besides the above pharmaceuticals, DNAs and proteins of the present invention as described above are also useful as reagents for research in the art. Furthermore, the above-described proteins of the present invention may be used as an active ingredient of diagnostic agents for tumors. Specifically, a tumor antigen protein of the present invention may be labeled, as needed, and used for detecting the presence of antibodies (antibodies against the tumor antigen protein) in a sample (such as blood, tumor tissue) obtained from a patient suspected to have a tumor, in order to diagnose the presence or absence of tumors. In addition, proteins of the present invention are also useful as an immunogen for producing antibodies of the present invention described below.

As used herein, the term "antibodies" refers to antibodies which are directed against a tumor antigen protein of the present invention or partial protein comprising part thereof. Such antibodies are easily prepared, for example, according to the method described in "Antibodies: A Laboratory Manual", Lane, H. D. et al. eds., Cold Spring Harbor Laboratory Press, New York, 1989. Specifically, antibodies of the present invention may easily be prepared using a tumor antigen protein of the present invention or partial protein comprising part thereof as an immunogen by immunizing an animal in a conventional manner. Examples of such immunogen are a tumor antigen proteins of the present invention, a partial protein comprising part of a tumor antigen protein of the present invention (including a peptide fragment), a fusion protein between a tumor antigen protein of the present invention or partial protein comprising part thereof and GST (glutathione S-transferase), and a fusion protein between a tumor antigen protein of the present invention or partial protein comprising part thereof and Myc tag. In this context, the length of partial protein will be typically at least 8 amino acids in light of the minimum length that can constitute an epitope.

In addition, monoclonal antibodies specific for a tumor antigen protein of the present invention can be prepared according to a known method. The hybridoma technique originally described by Kohler and Milstein, *Eur. J. Immunol.* 6, 511 (1976) has been applied to the production of monoclonal antibodies against many specific antigens, and may be practiced by those skilled in the art according to the procedures described in literatures such as "Bunshi-Seibutu-Gaku-Kennkyu-No-Tame-No-Tanpakushitu-Jikkenn-Ho" (Chapter 4, Yodosha, 1994)

The method and schedule for immunization of a host animal or for cultivation of antibody-producing cells obtained from the host animal are in accordance with conventional established antigen-stimulation and production techniques.

Antibodies obtained may be purified by known techniques including immunoaffinity chromatography, HPLC (high performance liquid chromatography) and the like.

Based on antibodies thus obtained, it is also possible to prepare various antibody fragments. Such antibody fragments include, for example, F(ab')$_2$ fragment which can be generated by pepsin digestion of an antibody, Fab' fragment which can be generated by reducing the disulfide bond in F(ab')$_2$ fragment, and 2Fab or Fab fragment which can be generated by treating an antibody with papain and a reducing agent, and such fragments are also within the scope of the present invention.

Furthermore, based on such antibodies or antibody fragments, it is also possible to prepare various derivatives. "Derivatives" as used herein include, for example, chimera antibodies and humanized antibodies, and such antibodies may be prepared, for example, according to the method described in the Japanese Patent Publication (Kokai) 61-47500 (1986) or *Nature* 321, 522 (1986). In addition, the above antibodies or antibody fragments labeled with, for example, an enzyme are also included within the scope of said derivatives. Specific examples of the enzyme labeling method include the glutaraldehyde method, the periodate method, the maleimide method, and the pyridyl-disulfide method. Examples of enzyme used as a label include bovine small intestine alkaline phosphatase and horseradish peroxidase. These labeled antibodies may easily be prepared by those skilled in the art according to a standard reference such as "Koso-Menneki-Sokutei-Ho" (Igaku-Shoin, 1978). Furthermore, radioisotopes may also be used as a label.

Antibodies, antibody fragments, or derivatives thereof as described above (hereinafter collectively referred to as "antibodies and the like") may be used as a diagnostic agent for tumors as described below.

As demonstrated below in Example 4, Western blot analysis on various cell lines and tissues using antibodies of the present invention revealed that expression of the novel tumor antigen protein of the present invention was observed in 100% of head and neck squamous cell cancers, 60% of esophageal squamous cell cancers, 50% of lung squamous cell cancers, and 50% of lung adenocarcinomas examined, although no expression was observed in any of all normal tissues except for testis and fetal liver, melanomas, and leukemia. Furthermore, it was also demonstrated that cancer cells positive in the above Western blot analysis (cancer cells expressing the tumor antigen protein of the present invention) are indeed recognized and damaged by tumor specific CTLs.

Thus, the tumor antigen protein of the present invention proved to be expressed specifically and with high frequency in various squamous cell carcinomas and adenocarcinomas, whereas no expression was detected in normal tissues except for testis and fetal liver, melanomas, or leukemias. Accordingly, it is believed that antibodies and the like against tumor antigen proteins of the present invention can be widely used in the diagnosis of patients with such cancers. Furthermore, by detecting tumor antigen proteins of the present invention with these antibodies and the like, it becomes possible to diagnose the development, recurrence and metastasis of tumors early, and to select efficiently tumor patients to whom pharmaceuticals containing tumor antigen proteins or peptides, or DNAs encoding the same of the present invention can be adapted. Consequently, they are expected to be very useful for treatment and prophylaxis of tumors.

The present invention thus provides antibodies against tumor antigen proteins of the present invention or against partial protein comprising part thereof, antibody fragments, or derivatives thereof.

The present invention also provides compositions for treatment or diagnosis of tumors that comprises as an active ingredient any one of such antibodies, antibody fragments, or derivatives.

The present invention further provides a method for diagnosis of tumors using antibodies or antibody fragments of the present invention or derivatives thereof.

Antibodies and the like of the present invention may be used as an active ingredient of diagnostic agents for tumors in an appropriate buffer such as phosphate buffer (pH 7.0) containing bovine serum albumin. Examples of immunological diagnosis using a diagnostic agent of the present invention include those wherein the tumor antigen protein is detected from tumor tissue samples or those wherein the presence of the tumor antigen protein in blood or a tissue is detected. More specific examples include an immunohistochemical method, immunoblotting, radioimmunoassay (RIA), enzyme-linked immunosorbent assay (ELISA), and a fluorescent or luminescent assay, as well as Western blot analysis described below in Example 4. The details of these assays are given in a standard reference such as "Koso-Menneki-Sokutei-Ho" (Igaku-Shoin, 1978).

Depending on the assay, diagnostic agents of the present invention can be used in the form of a kit which comprises enzyme-labeled antibodies, a coloring agent, a coloring aid, a stopping agent, a standard, and the like.

Treatment with antibodies and the like of the present invention can be conducted by a method wherein monoclonal antibody specific for tumor antigen protein of the present invention can be administered to a cancer patient as it is or as a conjugate with an anti-tumor agent or a toxin to kill the tumor cells expressing said tumor antigen protein.

Furthermore, antibodies and the like of the present invention is also usable in the affinity chromatography or the screening of cDNA library.

The following examples are provided to further illustrate the present invention and are not to be construed as limiting the scope thereof.

REFERENCE EXAMPLE 1

Establishment of Cytotoxic T Lymphocyte (CTL) Cell Line Against Esophageal Cancer Cell Line According to the disclosure of Nakao et al., *Cancer Res.*, 55:4248–4252 (1995), CTL against an esophageal cancer cell line, KE-4, belonging to squamous cell carcinomas when classified on the basis of the tissue type was established from peripheral blood monocytes of a patient, named KE-4CTL, and used in experiments. The esophageal cancer cell line KE-4 and KE-4CTL have been deposited at The National Institute of Bioscience and Human Technology (1-1-3 Higashi, Tsukuba, Ibaraki, Japan) under International Deposition Nos. FERM BP-5955 and FERM BP-5954, respectively, both on May 23, 1997. Furthermore, typing of HLA class I molecules of KE-4 was conducted according to the above-noted disclosure of Nakao et al., and it was confirmed that they are HLA-A2402, -A2601, B54, -B60, -Cwl, and -Cw3.

REFERENCE EXAMPLE 2

Preparation of HLA-A2601 cDNA

Using KE-4 described above, a recombinant plasmid was prepared by incorporating cDNA for HLA-A2601 into an expression vector pCR3 (INVITROGEN) according to the disclosure of Nakao et al., *Cancer Res.*, 55:4248–4252 (1995).

REFERENCE EXAMPLE 3

Preparation of cDNA Library Derived from KE-4

Poly $(A)^+$ mRNA was prepared from KE-4 by isolation of total RNA fraction and purification on oligo (dT) column using mRNA Purification system (manufactured by Pharmacia Biotech) according to the manufacturer's protocol. cDNAs having NotI adapter and Sca I adapter linked to each terminus were prepared from mRNAs using SuperScript™ Plasmid System (Gibco BRL) according to the manufacturer's protocol, which was then ligated to an expression vector, plasmid pSV-SPORT1 (Gibco BRL), which had been digested with restriction enzymes NotI and SalI to yield recombinant plasmids. The recombinant plasmids were introduced into *E. coli*. ElectroMAX DH10B/p3™ cells (Gibco BRL) using electric pulses in Gene Pulser (Bio-Rad) under conditions of 25 $\mu$F and 2.5 kV. Transformants into which the recombinant plasmids had been introduced were selected in LB medium (1% bacto-trypton, 0.5% yeast extract, 0.5% NaCi, pH7.3) containing ampicillin (50 $\mu$g/ml).

REFERENCE EXAMPLE 4

Quantitative Determination of Interferon-γ

Quantitative Determination of interferon-γ (IFN-γ) was conducted by enzyme immunoassay (ELISA). An anti-human IFN-γ mouse monoclonal antibody was adsorbed on wells of 96-well microplate as a solid-phased antibody, and after blocking non-specific bindings with bovine serum albumin, allowed to bind with IFN-γ in samples. Anti-human IFN-γ rabbit polyclonal antibody as a detection antibody was then allowed to bind, and after binding with an anti-rabbit immunoglobulin goat antibody labeled with alkaline phosphatase, reacted with para-nitrophenyl phosphate as a chromogenic substrate. After quenching the reaction by adding an equal volume of 1N NaOH, absorbance at 405 nm was measured. The absorbance was compared with that obtained with standard IFN-γ to determine the amount of IFN-γ in the supernatant.

EXAMPLE 1

Screening of Gene for Novel Tumor Antigen Protein

The recombinant plasmid DNAs were recovered from pools of about 100 transformants described in Reference Example 3 as follows. A hundred transformants were introduced and cultured in each well of 96-well U-bottomed microplate containing LB medium plus ampicillin (50 µg/ml). Part of the culture was then transferred to another 96-well U-bottomed microplate containing 0.25 ml per well of TYGPN medium (F. M. Ausubel et al., *Current Protocols in Molecular Biology*, John Wiley & Sons, Inc.), and cultured for 48 hours at 37° C. The remaining cultures in LB medium on the microplate were stored in frozen. Preparation of recombinant plasmid DNAs from transformants cultured in TYGPN medium was achieved in the microplate by alkaline lysis (F. M. Ausubel et al., *Current Protocols in Molecular Biology*, John Wiley & Sons, Inc.). The recombinant plasmid DNAs recovered by isopropanol precipitation were suspended in 50 µl of 10 mM Tris, 1 mM EDTA, pH 7.4, containing 20 ng/ml RNase.

Fibroblast cell line, VA-13 cells (RIKEN CELL BANK, The Institute of Physical and Chemical Research; *Ann. Med. Exp. Biol. Fenn.*, 44:242–254, 1966) were doubly transfected with the recombinant plasmid for KE-4 cDNA and the recombinant plasmid for HLA-A2601 cDNA using Lipofectin method as follows. Seven thousands VA-13 cells were placed in each well of 96-well flat-bottomed microplate, and incubated for 2 days in 100 µl of RPMI 1640 medium containing 10% FCS. Using Lipofectin reagent (Gibco BRL), 30 µl of 70 µl mixture consisting of 25 µl of the recombinant plasmid for KE-4 cDNA corresponding to about 100 transformants, 10 µl (200 ng) of the recombinant plasmid for HLA-A2601 cDNA described in Reference Example 2, and 35 µl of about 35-fold diluted Lipofectin reagent was added to VA-13 cells to be doubly transfected. Transfectants were prepared in duplicate. After 5 hours, 200 µl of culture medium containing 10% FCS was added to the transfectants, and further incubated for 72 hours at 37° C. After removing the culture medium, 10,000 KE-4CTL cells were added to each well, and cultured for 24 hours at 37° C. in 100 µl of culture medium containing 10% FCS and 25 U/ml IL-2. The culture medium was recovered, and measured for IFN-γ by ELISA.

Regarding four groups in which high production of IFN-γ was observed, corresponding frozen-stored pools of about 100 transformants containing recombinant plasmids for KE-4 cDNA were used in the following screening. The pools of the transformants were plated on LB agar medium containing ampicillin (50 µg/ml) to obtain colonies. Two hundreds colonies for each group (total 800 colonies) were cultured as described above so that a single kind of transformant is included in each well, thereby recombinant plasmid DNAs for KE-4 cDNA were prepared. Then, VA-13 cells were doubly transfected with the recombinant plasmid for KE-4 cDNA and the recombinant plasmid for HLA-A2601 cDNA followed by cocultivation with KE-4CTL, and IFN-γ produced due to KE-4CTL reaction was quantitatively determined as described above in order to select positive plasmids. In this manner, a KE-4 cDNA recombinant plasmid clone was selected. Furthermore, similar procedures were repeated with said plasmid clone to determine the amount of IFN-γ produced by KE-4CTL according to the method of Reference Example 4. The results are shown in FIG. 1. A similar experiment was conducted using HLA of a different type (HLA-A0201) for comparison. In the Figure, ■ and □ indicate the results obtained by HLA-A2601 cDNA and HLA-A0201 cDNA, respectively. The horizontal axis indicates the amount of the above plasmid clone (ng/well), and the vertical axis indicates the amount of IFN-γ (pg/ml) produced by KE4-CTL. It was demonstrated by FIG. 1 that the transfection of VA-13 cells with this plasmid clone induces production of IFN-γ from KE-4CTL, that is, the plasmid clone represents a gene encoding a tumor antigen protein.

EXAMPLE 2

Determination of Base Sequence of Novel Tumor Antigen Protein Gene

Transformants containing the recombinant plasmid selected in Example 1 into which cDNA for the tumor antigen protein gene had been incorporated were cultured for 14 to 16 hours at 37° C. in 500 ml of LB medium containing ampicillin (50 µg/ml), and the bacterial cells were harvested by centrifugation. The recombinant plasmid was recovered from the cells using PLASMID MAXI kit (QIAGEN). The cDNA has been incorporated into a site located between SP6 RNA polymerase promoter sequence and T7 RNA polymerase promoter sequence. The SP6 promoter primer and T7 promoter primer described in the literature (*DNA* 4:165, 1985) were then synthesized. The dideoxy sequencing reaction was conducted using SP6 promoter primer or T7 promoter primer in combination with Fluore-dATP Labeling Mix (Pharmacia Biotech) and Auto-Read Sequencing Kit (Pharmacia Biotech), and the base sequence of the cDNA was determined from the both termini using a fluorescence DNA sequencer (Pharmacia Biotech). The base sequence thus determined (1011 bp) is shown in SEQ ID NO: 1. The base sequence shown in SEQ ID NO: 1 corresponds to the sequence at and after position 1517 of DNA encoding the tumor antigen protein, SART-1, described in the International Publication WO 97/46676 (shown as SEQ ID NO: 2 in WO 97/46676).

EXAMPLE 3

Production of Antibody Against Novel Tumor Antigen Protein

A recombinant plasmid into which cDNA for the novel tumor antigen protein gene obtained in Example 2 had been incorporated was amplified by PCR using two primers:

sf-1: 5'-TGGGAATTCGATGAGGATCCCGAGC-3' sr-1: 5'-TACGGGCGGCCGCTGTCACTTGGT-3'.

This amplified fragment has a partial sequence corresponding to positions 146 to 930 of the base sequence shown in SEQ ID NO: 1.

The amplified fragment was cleaved with restriction enzymes EcoRI and NotI, and ligated into EcoRI and NotI sites of a plasmid vector pGEX-5X-3 (Pharmacia Biotech), which expresses a fusion protein with glutathione S-transferase, to obtain a recombinant plasmid. The recombinant plasmid was introduced into *E. coli* strain DH5α, and transformants were selected. The transformants were cultured in a large scale, and the bacterial cells were disrupted by sonication in the presence of protease inhibitors PMSF and aprotinin to extract the fusion protein between the tumor antigen protein of the present invention and GST. The fusion protein was then isolated by affinity purification using Glutathione Sepharose 4B (Pharmacia Biotech) and gel filtration using Superrose 12 (Pharmacia Biotech). The isolated fusion protein was used as an antigen to immunize a rabbit in a conventional manner to yield antiserum.

EXAMPLE 4

Western Blot Analysis

Expression of the tumor antigen protein of the present invention in various cell lines and tissues was investigated by Western blotting using the antiserum obtained in Example 3.

Each of various cell lines and tissues was lysed by sonication in 10 mM Tris-HCl, pH 7.4, 150 mM NaCl, and 0.5% Triton X-100, containing 0.03 TIU/ml aprotinin. The lysate was centrifuged for 20 minutes at 14,000 rpm and the supernatant was subjected to SDS-PAGE. The proteins thus separated were transferred onto Hybond-PVDF membrane (Amersham) and incubated with an appropriate amount of the antiserum obtained in Example 3 for 4 hours at room temperature. Other details of the Western blotting procedure were in accordance with the method described in Shichijo et al., *Journal of Immunological Methods*, 186:137 (1995).

Figure 2:
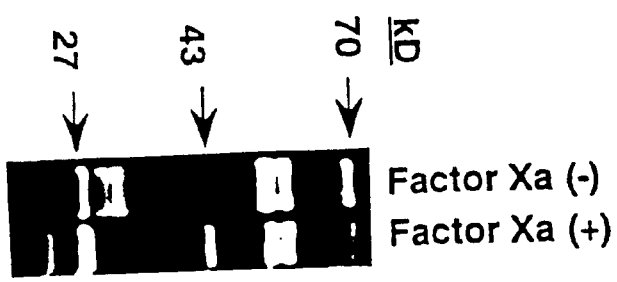
FIG. 2 shows the results of electrophoresis in Western blotting conducted using an antiserum against a fusion protein (about 70 kD) between the novel tumor antigen protein (about 43 kD) of the present invention and GST (about 27 kD).
Figure 2:
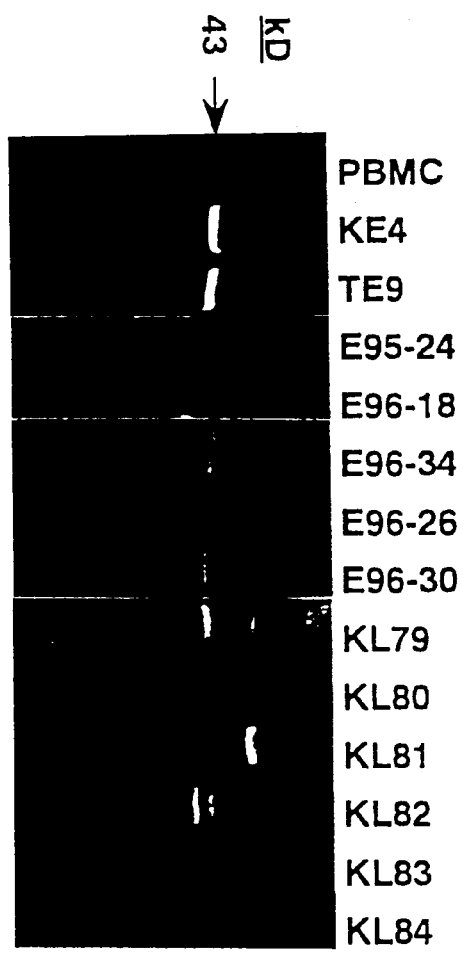

The results are shown in FIG. 2. The antiserum obtained in Example 3 recognized a fusion protein of 70 kDa used for immunization. The antiserum also recognized the both tumor antigen protein of 43 kDa and GST of 27 kDa (FIG. 2A) which were resulted from the cleavage of fusion protein with an enzyme, factor X. The investigation regarding expression of the tumor antigen protein in various cells and tissues revealed that, in cells, expression was not detected any of five healthy human peripheral blood monocytes (PBMC), 16 leukemia cell lines, and 2 melanoma cell lines studied, but was observed in 3 out of 5 head and neck squamous cell carcinoma cell lines, 4 out of 6 esophageal squamous cell carcinoma cell lines, all of 3 lung squamous cell carcinoma cell lines, and 3 out of 6 lung adenocarcinoma cell lines examined. In normal tissues, expression was observed in all of 1 fetal liver and 3 testes studied, but it was not detected in all of 1 newborn liver, 1 adult liver, 2 uteri, 4 esophagi, and 1 pancreas examined. In cancer tissues, expression was not detected in any of 10 leukemias and 10 melanomas, but it was observed in 7 out of 7 head and neck squamous cell carcinomas, 18 out of 30 esophageal squamous cell carcinomas, 8 out of 17 lung squamous cell carcinomas, and 16 out of 35 lung adenocarcinomas. Some examples of the results are shown in FIG. 2(B). As described just above, the novel tumor antigen protein of the present invention proved to be expressed specifically and with high frequency in various squamous cell carcinomas and adenocarcinomas, and, therefore, the antibodies against the novel tumor antigen protein of the present invention are believed to be applicable to diagnoses of such cancer cells and cancer patients.

EXAMPLE 5

Expression of Tumor Antigen Protein in Various Cancer Cells and Measurement of Cytotoxic Activity of CTL The recombinant plasmid (K3) (FERM BP-5951) containing the base sequence described in SEQ ID NO: 2 of WO 97/46676 was treated with EcoRI and NotI to obtain a DNA fragment, which fragment was inserted into EcoRI and NotI sites of a plasmid vector pGEX-4T-2 (Pharmacia Biotech) for the expression of a fusion protein with glutathione S-transferase (GST) to obtain a recombinant plasmid. A fusion protein with GST and an antiserum against the protein was prepared using the plasmid in a manner similar to that described in Example 3. The resultant antiserum recognizes the tumor antigen-protein of molecular weight of about 125 kDa described in WO 97/46676. Western blotting was conducted using the said antiserum against about 125 kDa protein and the antiserum against about 43 kDa protein which was obtained in Example 3 and directed to the tumor antigen protein of the present invention to examine expression in various HLA-A24-positive cancer cell lines in accordance with the procedures described in Example 4. On the other hand, cytotoxicity (specific lysis) of KE-4CTL on various cancer cells was measured according to the method described in D. D. Kharkevitch et al., *Int. J. Cancer*, 58:317 (1994), wherein $2\times10^5$ KE-4CTLs was reacted with $10^4$ target cancer cells labeled with $^{51}$Cr. The results are shown below in Table 1.

TABLE 1

| Cell lines | Origin | Expression of protein | | Specific lysis (%) |
|---|---|---|---|---|
| | | 43 kD | 125 kD | |
| KE-4 | esophageal cancer | + | + | 27 |
| KE-3 | esophageal cancer | + | + | 32 |
| TE-8 | esophageal cancer | + | + | 23 |
| TE-11 | esophageal cancer | + | + | 31 |
| PC9 | lung cancer | + | + | 39 |
| 11–18 | lung cancer | + | + | 27 |
| SKG-1 | uterine cancer | + | + | 25 |
| TE-10 | esophageal cancer | − | + | 38 |
| LU65A | lung cancer | − | + | 6 |
| PERF-LC-AI | lung cancer | − | + | 3 |
| LK79 | lung cancer | − | + | 3 |

\* + indicates that a corresponding band was visible on the Western blots, whereas - indicates that no corresponding band was observed.

As shown in Table 1, expression of the 125 kDa protein was observed in all cancer cells examined. Among these cell lines, KE-4CTL exerted cytotoxic effect on those expressing the 43 kDa protein. KE-4CTL, however, did not exerted the toxic effect on cancer cell lines not expressing the 43 kDa protein except for TE-10. These results indicate that antigen peptides derived from the 43 kDa protein have a tendency to be presented as an antigen and recognized by CTL more efficiently than antigen peptides derived from the 125 kDa protein. In conclusion, the antibodies against the 43 kDa protein are much more useful in the diagnoses of cancer patients who can be treated effectively with the tumor antigen proteins of the present invention, tumor antigen peptides thereof, or DNAs encoding the tumor antigen proteins.

INDUSTRIAL APPLICABILITY

The novel tumor antigen proteins of the present invention, which are expressed in various squamous cell carcinomas or adenocarcinomas with high frequency, genes encoding the same, and antibodies against the novel tumor antigen proteins are useful in prophylaxis, treatment, or diagnosis of a wide range of tumors.

SEQUENCE LISTING

<160> NUMBER OF SEQ ID NOS: 4

<210> SEQ ID NO 1
<211> LENGTH: 1011
<212> TYPE: DNA
<213> ORGANISM: Homo sapiens

<400> SEQUENCE: 1

```
cgaggcggag ctggagctgc agaagcagct ggagaaggga cgccggctgc gacagttaca      60
gcagctacag cagctgcgag acagtggcga gaaggtggtg gagattgtga agaagctgga     120
gtctcgccag cggggctggg aggaggatga ggatcccgag cggaagggg ccatcgtgtt      180
caacgccacg tccgagttct gccgcacctt gggggagatc cccacctacg ggctggctgg     240
caatcgcgag gagcaggagg agctcatgga ctttgaacgg gatgaggagc gctcagccaa     300
cggtggctcc gaatctgacg gggaggagaa catcggctgg agcacggtga acctggacga     360
ggagaagcag cagcaggatt tctctgcttc ctccaccacc atcctggacg aggaaccgat     420
cgtgaatagg gggctggcag ctgccctgct cctgtgtcag aacaaagggc tgctggagac     480
cacagtgcag aaggtggccc gggtgaaggc ccccaacaag tcgctgccct cagccgtgta     540
ctgcatcgag gataagatgg ccatcgatga caagtacagc cggagggagg aataccgagg     600
cttcacacag gacttcaagg agaaggacgg ctacaaaccc gacgttaaga tcgaatacgt     660
ggatgagacg ggccggaaac tcacacccaa ggaggctttc cggcagctgt cgcaccgctt     720
ccatggcaag ggctcaggca agatgaagac agagcggcgg atgaagaagc tggacgagga     780
ggcgctcctg aagaagatga gctccagcga cacgcccctg gcaccgtgg ccctgctcca     840
ggagaagcag aaggctcaga agacccccta catcgtgctc agcggcagcg gcaagagcat     900
gaacgcgaac accatcacca gtgacagcg cctcccgta gtcggccctg cctcaacctt      960
catattaaat aaagctccct ccttattttt aaaaaaaaaa aaaaaaaaaa a             1011
```

<210> SEQ ID NO 2
<211> LENGTH: 111
<212> TYPE: PRT
<213> ORGANISM: Homo sapiens

<400> SEQUENCE: 2

```
Glu Tyr Arg Gly Phe Thr Gln Asp Phe Lys Glu Lys Asp Gly Tyr Lys
1               5                   10                  15
Pro Asp Val Lys Ile Glu Tyr Val Asp Glu Thr Gly Arg Lys Leu Thr
            20                  25                  30
Pro Lys Glu Ala Phe Arg Gln Leu Ser His Arg Phe His Gly Lys Gly
        35                  40                  45
Ser Gly Lys Met Lys Thr Glu Arg Arg Met Lys Lys Leu Asp Glu Glu
    50                  55                  60
Ala Leu Leu Lys Lys Met Ser Ser Ser Asp Thr Pro Leu Gly Thr Val
65                  70                  75                  80
Ala Leu Leu Gln Glu Lys Gln Lys Ala Gln Lys Thr Pro Tyr Ile Val
                85                  90                  95
Leu Ser Gly Ser Gly Lys Ser Met Asn Ala Asn Thr Ile Thr Lys
            100                 105                 110
```

<210> SEQ ID NO 3
<211> LENGTH: 25
<212> TYPE: DNA

```
<213> ORGANISM: Artificial
<220> FEATURE:
<223> OTHER INFORMATION: Artificial primer derived from Homo sapiens
      used to amplify a fragment with a partial sequence corresponding
      to positions 146 to 930 of the base sequence shown in SEQ ID
      NO: 1

<400> SEQUENCE: 3
tgggaattcg atgaggatcc cgagc                                           25

<210> SEQ ID NO 4
<211> LENGTH: 24
<212> TYPE: DNA
<213> ORGANISM: Artificial
<220> FEATURE:
<223> OTHER INFORMATION: Artificial primer derived from Homo sapiens
      used to amplify a fragment with a partial sequence corresponding
      to positions 146 to 930 of the base sequence shown in SEQ ID NO: 1

<400> SEQUENCE: 4
tacgggcggc cgctgtcact tggt                                            24
```

What is claimed is:

1. An isolated nucleic acid consisting of the nucleotide sequence shown in SEQ ID NO:1.

2. An isolated expression plasmid comprising the nucleic acid of claim 1.

3. An isolated transformant transformed with the expression plasmid of claim 2.

4. An isolated tumor antigen protein produced through the expression of the nucleic acid of claim 1.

5. A process for producing a recombinant protein, comprising culturing the transformant of claim 3 under conditions sufficient for the production of said protein, whereby said recombinant protein is produced, and recovering the recombinant protein.

6. The process of claim 5, wherein said process further comprises recovering said recombinant protein.

* * * * *